United States Patent [19]

Itonaga et al.

[11] Patent Number: 4,653,924

[45] Date of Patent: Mar. 31, 1987

[54] ROTATING ANALYZER TYPE ELLIPSOMETER

[75] Inventors: Makoto Itonaga; Kanji Kayanuma, both of Kanagawa, Japan

[73] Assignee: Victor Company of Japan, Ltd., Japan

[21] Appl. No.: 742,988

[22] Filed: Jun. 10, 1985

[30] Foreign Application Priority Data

Jun. 12, 1984 [JP] Japan .................................. 59-121377
Jun. 15, 1984 [JP] Japan .................................. 59-123314

[51] Int. Cl.$^4$ ............................................. G01J 4/00
[52] U.S. Cl. ..................................... 356/369; 356/364
[58] Field of Search ............... 356/369, 367, 364, 381, 356/388

[56] References Cited

U.S. PATENT DOCUMENTS 4,105,338  8/1978  Kuroha .............................. 356/369

OTHER PUBLICATIONS

"The Application of Intensity Transients in Ellipsometry" Brusic et al. *Applied Optics*, vol. 9, #7, 7/1970, pp. 1634–1639.

"A Digital Ellipsometer" Abe et al. *Japanese Journal of Applied Optics*, vol. 18, #1, 1/1979, pp. 165–167.

"High Precision Scanning Ellipsometer" Aspnes et al. *Applied Optics* vol. 14, #1, 1/1975, pp. 220–228.

*Primary Examiner*—R. A. Rosenberger
*Assistant Examiner*—Crystal D. Cooper
*Attorney, Agent, or Firm*—Andrus, Sceales, Starke & Sawall

[57] ABSTRACT

A rotating analyzer type ellipsometer comprises a rotating analyzer for receiving light which is impinged on a sample with a predetermined incident angle and reflected by the sample, a rotary phase detecting apparatus provided so as to rotate unitarily with the rotating analyzer for generating a rotary phase signal as the rotary phase detecting apparatus rotates, a rotating mechanism for rotating the rotating analyzer and the rotary phase detecting apparatus, a photodetector for producing an output responsive to light which is passed through the rotating analyzer, and a computer for obtaining a phase difference between the rotating analyzer and the rotary phase detecting apparatus from a phase difference $\phi_o$ with which a difference between an output $I_p$ of the photodetector and a theoretical value $I_o$ becomes a minimum or substantially zero by entering into the computer the output $I_p$ of the photodetector and calculating the theoretical value $I_o$ while changing the values of the output $I_p$ and an initial value $\phi_o$ of the phase difference.

5 Claims, 6 Drawing Figures

ROTATING ANALYZER TYPE ELLIPSOMETER

BACKGROUND OF THE INVENTION

The present invention generally relates to rotating analyzer type ellipsometers, and more particularly to an ellipsometer which detects a phase difference between a rotating analyzer and a rotary phase detecting apparatus (rotary encoder) and sets an initial value for measurement calculations of an optical constant, film thickness and the like.

Generally, an ellipsometer which measures the ellipticity of the polarized light by use of ellipsometry, has been used conventionally when measuring the film thickness of a sample, for example. The ellipsometer is used for such a measurement because the sample will not be destroyed and it is possible to measure with a high accuracy the optical constant of the sample and the film thickness of an extremely thin single layer film by observing the change in the polarization state of the reflected light from the sample. An ellipsometer which employs a rotating analyzer is often used as an ellipsometer for performing such a measurement.

A general film thickness measuring apparatus which uses the polarization analysis method as the operating principle thereof, impinges light from a light source on a measuring plate with an arbitrarily selected incident angle. The measuring plate is formed with a transparent film on top of a transparent substrate, and the thickness of the transparent film is to be measured. The light reflected from the measuring plate is detected in an ellipsometer of the film thickness measuring apparatus, and a detection output of the ellipsometer is analyzed in an analyzer system so as to measure the film thickness of the transparent film.

In this type of a film thickness measuring apparatus, the film thickness is not measured immediately. First, an amplitude ratio tan $\psi$ and a phase difference $\Delta$ between two mutually perpendicular polarized light components of the reflected light which is obtained when the incident light is reflected by the measuring plate, are compared. On the other hand, different values for the film thickness are successively substituted into a predetermined equation which has a film thickness d as the parameter, so as to obtain the amplitude ratio and the phase difference between the two polarized light components by calculation. It is assumed that the value for the film thickness d which is substituted into the predetermined equation is the thickness of the transparent film which is measured, when the calculated amplitude ratio and the calculated phase difference are equal to the measured amplitude ratio and the measured phase difference, respectively (with an error within a tolerance).

In the ellipsometer, the light impinged on the sample surface with a predetermined incident angle and reflected thereby is impinged on the rotating analyzer which is provided coaxially to the rotary encoder, and the light from the rotating analyzer is received by a photodetector. The incident angle with which the light is impinged on the sample surface must accurately coincide with the predetermined incident angle. Further, the accurate phase difference between the rotating analyzer and the rotary encoder must be known. These conditions must be satisfied because it is necessary to first set an initial value for the measurement calculation by use of the phase difference between the rotating analyzer and the rotary encoder when starting the measurement of the optical constant, film thickness and the like.

However, in an optical system in which the incident angle is fixed, there is no known method of measuring the phase difference between the rotating analyzer and the rotary encoder provided in the optical system. Hence, in the conventional ellipsometer, the phase difference between the rotating analyzer and the rotary encoder is detected by impinging the light from the light source directly on the rotating analyzer without by way of a reflecting surface. The light is a linearly polarized light of which polarization state is known.

But even in the case of the ellipsometer in which the phase difference between the rotating analyzer and the rotary encoder is detected by impinging directly on the rotating analyzer without by way of the reflecting surface the light from a laser light source which emits a linearly polarized light the polarization state of which is known, the light from the laser light source must be impinged on the sample surface with an incident angle accurately coinciding with the predetermined incident angle and the reflected light from the sample surface must be correctly impinged on the rotating analyzer through a pinhole, when the detected phase difference is to be used for the actual measurement. Accordingly, the mounting angles of a part including the light source and a part including the rotating analyzer must be set to respective desired mounting angles with an extremely high accuracy, from a state where the phase difference between the rotating analyzer and the rotary encoder is detected by impinging on the rotating analyzer the light from the light source without by way of the reflecting surface and with optical axes of the two parts coinciding, to a state where the light from the light source is impinged on the sample surface with the predetermined incident angle. But there are disadvantages in that such setting and adjustment are troublesome and difficult to perform. Moreover, mechanisms for permitting the mounting angles of the two parts to be variably adjusted with such a high accuracy, become complex and must be precise. As a result, the degree of freedom with which the designing may be carried out becomes poor, and the manufacturing cost becomes high. In addition, the mounting angles may become out of order and deteriorate the measuring accuracy. Further, there is a disadvantage in that a difficult operation of matching the optical axes of the two parts must be carried out when replacing a worn-out part.

On the other hand, according to the conventional film thickness measuring apparatus, when the amplitude ratio and the phase difference of the two polarized light components are taken along the X and Y coordinates and the film thickness is obtained with respect to the amplitude ratio and the phase difference is plotted, the collection of the plots form an oval shape. Thus, two values for the film thickness exist with respect to one phase difference, for example. For this reason, the film thickness cannot be obtained solely from the phase difference, and the film thickness must always be obtained from the amplitude ratio and the phase difference. Further, even when the amplitude ratio and the phase difference change slightly in value, the value of the film thickness which is obtained changes greatly. As a result, there are disadvantages in that the film thickness measuring accuracy is poor, and that it takes a considerably long time to perform calculations and the like for obtaining the film thickness.

Accordingly, the prevent inventors have previously proposed in a U.S. patent application Ser. No. 736,938 entitled "Film Thickness Measuring Apparatus" a film thickness measuring apparatus which impinges light from a light source on a transparent film with an incident angle $\theta$ equal to or approximately equal to a polarizing angle $\theta$ ($\theta=\tan^{-1} n$) which is determined by the refractive index n of the transparent film and measures light reflected by the transparent film. As will be described later on in the present specification, the present invention is suited for application to this previously proposed film thickness measuring apparatus.

Further, in a conventional rotating analyzer type ellipsometer, the axes of rotation of the rotating analyzer and the rotary encoder are independent of each other. In this conventional rotating analyzer type ellipsometer, the rotational force is transmitted from a rotary shaft of a motor to rotary shafts of the rotating analyzer and the rotary encoder by use of gears or timing belts, for example, since the axes of rotation of the rotating analyzer and the rotary encoder are independent of each other. In the case where the rotational force is transmitted by use of gears, an error is introduced between the rotary angle of the rotating analyzer and the rotary angle of the rotary encoder due to eccentricity and backlash of the gears. On the other hand, in the case where the rotational force is transmitted by use of timing belts, an error is introduced between the rotary angle of the rotating analyzer and the rotary angle of the rotary encoder due to the expansion and contraction of the timing belts. For these reasons, it is conventionally impossible to obtain a highly accurate measured result, and there was a demand for eliminating this problem.

SUMMARY OF THE INVENTION

Accordingly, it is a general object of the present invention to provide a novel and useful rotating analyzer type ellipsometer which can set the initial value described before.

Another and more specific object of the present invention is to provide a rotating analyzer type ellipsometer which detects the phase difference between a rotating analyzer and a rotary encoder and sets an initial value.

Still another object of the present invention is to provide a rotating analyzer type ellipsometer suited for use in the previously proposed film thickness measuring apparatus in which light is impinged on a transparent film with an incident angle $\theta$ set equal to a polarizing angle ($\theta=\tan^{-1} n$) which is determined by a refractive index n of the transparent film the thickness of which is to be measured.

A further object of the present invention is to provide a rotating analyzer type ellipsometer in which the rotating analyzer and the rotary encoder are provided coaxially.

Other objects and further features of the present invention will be apparent from the following detailed description when read in conjunction with the accompanying drawings.

DETAILED DESCRIPTION

Figure 1:
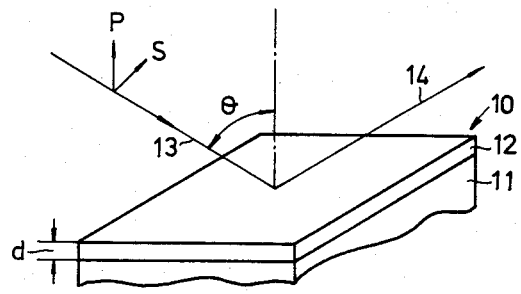
FIG. 1 is a diagram for explaining a measuring plate and the polarized light.

First, a description will be given with respect to a measuring plate the thickness of which is to be measured by a film thickness measuring apparatus applied with the ellipsometer according to the present invention, and an incident angle of light impinging on the measuring plate, by referring to FIG. 1.

A measuring plate 10 comprises a transparent film 12 formed on top of a transparent substrate 11. The transparent film 12 has a thickness d which is to be measured. When incident light 13 is impinged on the measuring plate 10 with an incident angle $\theta$, a part of the incident light 13 is reflected by the surface of the transparent film 12. The remaining part of the incident light 13 enters within the transparent film 12 and is reflected by the surface of the transparent substrate 11, and is then directed out of the transparent film 12 as reflected light 14. When a direction including the incident plane of light is represented by P (P-axis) and a direction perpendicular to the direction P is represented by S (S-axis), the polarization state of light can be described by a superposition of vibrations of light in two planes in the directions P and S.

For example, the transparent film 12 of the measuring plate 10 is a photoresist film which is formed on top of the transparent substrate 11. The transparent substrate 11 is a glass substrate, for example. The extinction coefficient (k) of the transparent film 12 and the transparent substrate 11 is equal to zero or an extremely small value.

The reflected light 14 is subjected to the effects of the thin film interference. Thus, when a Fresnel reflection coefficient of the measuring plate 10 with respect to the incident light 13 having the plane of vibration in the direction P is represented by $R_p$ and a Fresnel reflection coefficient of the measuring plate 10 with respect to the incident light 13 having the plane of vibration in the direction S is represented by $R_s$, the reflection coefficients $R_p$ and $R_s$ are dependent on the film thickness d. In other words, the reflection coefficients $R_p$ and $R_s$ are described by Fresnel reflection coefficients of air, the transparent film 12, and the transparent substrate 11. The reflection coefficients $R_p$ and $R_s$ can be described by the following complex numbers when equations describing the Fresnel reflection coefficients are substituted into the reflection coefficients $R_p$ and $R_s$.

$$R_p = r_p \exp(i\Delta_p) \tag{1}$$

$$R_s = r_s \exp(i\Delta_s) \tag{2}$$

The above equations (1) and (2) indicate that with respect to the incident light 13, the amplitude of the reflected light 14 becomes $r_p$ times and $r_s$ times and the phase of the reflected light 14 shifts by $\Delta_p$ and $\Delta_s$ in the directions P and S, respectively. A ratio of the reflection coefficients $R_p$ and $R_s$ can be described by the following equation (3).

$$R_p/R_s = [r_p\exp(i\Delta_p)]/[r_s\exp(i\Delta_s)] \quad (3)$$

$$= (r_p/r_s)\exp[i(\Delta_p - \Delta_s)]$$

The following equation (4) is obtained when $r_p/r_s = \tan \psi$ and $\Delta_p - \Delta_s = \Delta$ are substituted into the equation (3).

$$R_p/R_s = \tan \psi \exp(i\Delta) \quad (4)$$

The term $\tan \psi$ describes a ratio of the amplitudes of the polarized light components of the reflected light 14 in the directions P and S, and the term $\Delta$ describes a phase difference between the polarized light components in the directions P and S. Since the reflection coefficients $R_p$ and $R_s$ are dependent on the film thickness d, the ratio $R_p/R_s$ is also dependent on the film thickness d.

In order to obtain the film thickness d, the reflected light 14 is detected, and the amplitude ratio $\tan \psi$ and the phase difference $\Delta$ are measured in a conventionally known analyzing system. A ratio of the reflection coefficients is obtained by substituting the measured values into the equation (4). On the other hand, an arbitrary value for the film thickness d is substituted into an equation which is obtained by obtaining the real number portion of the equation (4) (this equation includes the film thickness d as a parameter), and the value which is obtained is compared with the value which is obtained by substituting the measured values. When the two values are not equal to each other, different values for the film thickness d are successively substituted into the equation until the two values become equal to each other with the error being within a tolerance. The value of the film thickness d which is substituted into the equation when the two values become equal to each other, is the value of the film thickness which is to be obtained.

In the previously proposed film thickness measuring apparatus described before, the incident angle $\theta$ of the incident light 13 is selected to $\theta = \tan^{-1} n$ for the reasons described in detail in the specification of the previously filed application, where n is the refractive index of the transparent film 12.

Figure 2:
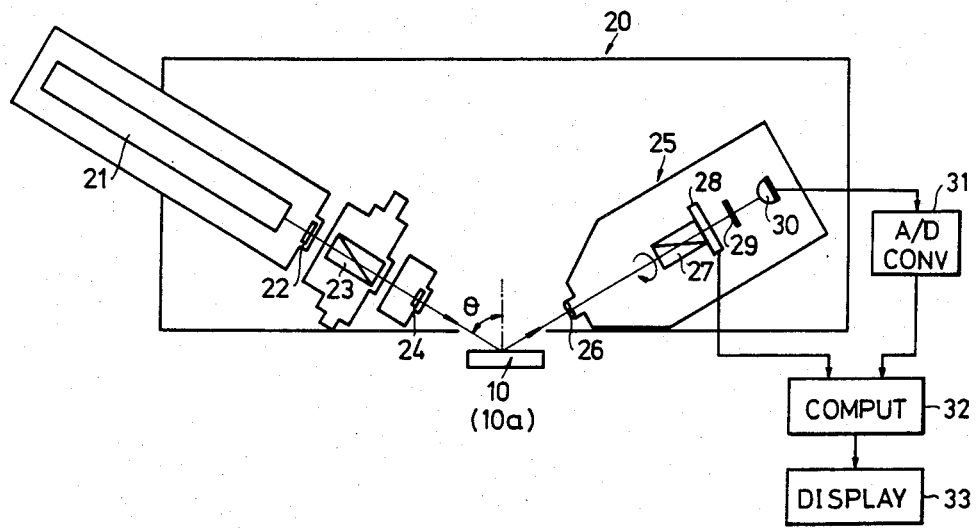
FIG. 2 generally shows an embodiment of a film thickness measuring apparatus applied with the rotating analyzer type ellipsometer according to the present invention.

A film thickness measuring apparatus having the incident angle selected in such a manner, is shown in FIG. 2. A film thickness measuring apparatus 20 comprises a light source 21 comprising a HeNe laser, for example. Laser light from the light source 21 is successively passed through a $\lambda/4$ plate 22, a polarizer (for example, a Glan-Thompson prism) 23, and a $\lambda/4$ plate 24, and is impinged on the upper surface of the measuring plate 10 with the incident angle $\theta$. The light source 21, the $\lambda/4$ plates 22 and 24, and the polarizer 23 are unitarily placed on a support (not shown). The support is set so that the light from the light source 21 impinges on the measuring plate 10 with the incident angle $\theta = \tan^{-1} n$ as described before.

The incident light is reflected by the measuring plate 10 and is subjected to the thin film interference. The reflected light is directed towards an ellipsometer 25. The ellipsometer 25 comprises a pinhole plate 26, a rotating analyzer 27, a rotary encoder 28, a pinhole plate 29, and a photodetector 30. The rotating analyzer 27 rotates together with the rotary encoder 28, and the reflected light is subjected to a time base conversion by the rotating analyzer 27. Hence, a time-sequential output is obtained from the photodetector 30.

A Glan-Thompson prism is used for the rotating analyzer 27, for example. The rotating analyzer 27 and the rotary encoder 28 are provided coaxially so as to rotate unitarily at a predetermined rotational speed (for example, several hundred rotations per minute), and an embodiment of a concrete construction thereof will be described later in conjunction with FIGS. 5A and 5B. The light passed through the rotating analyzer 27, passes through a hollow part of the rotary encoder 28 and reaches the photodetector 30. The photodetector 30 comprises a silicon photodiode, for example.

The output of the photodetector 30 is converted into a digital signal in an analog-to-digital (A/D) converter 31. The output digital signal of the A/D converter 31 is supplied to a computer 32 wherein the predetermined calculation described before is performed so as to measure the film thickness d. At the same time, the output signal of the rotary encoder 28 is supplied to the computer 32 as a timing signal. The measured result is displayed on a display 33.

However, it is difficult to make the direction (direction of a reference phase point) of the rotating analyzer 27 coincide with the direction of a reference phase point of the rotary encoder 28 when unitarily assembling the rotating analyzer 27 and the rotary encoder 28, and the rotating analyzer 27 and the rotary encoder 28 are assembled without making the directions of the reference phase points thereof coincide with each other. Accordingly, there is a phase difference between the rotating analyzer 27 and the rotary encoder 28. When the calculation is performed in the computer 32 in the state where the phase difference exists, it is impossible to measure the correct film thickness. Hence, it is necessary to know the phase difference and set an initial value when performing the calculation in the computer 32.

Hence, prior to starting the measurement of the film thickness, the phase difference is measured and an initial value is set as will be described hereinafter. First, a substrate 10a having a refractive index n approximately equal to the refractive index of the measuring plate 10, is positioned in place of the measuring plate 10. When the incident angle is equal to 58°, for example, a glass plate having a refractive index n of 1.6003 may be used for the substrate 10a.

The polarization state of the light reflected by the substrate 10a and reaching the rotating analyzer 27 is specified. The intensity $I_o$ of light after the light has passed through the rotating analyzer 27 with reference to a direction perpendicular to the measuring plate 10, can be described by $I_o = \sin^2 \omega t$ when the amplitude is assumed to be unity, where $\omega$ represents the angular velocity of the rotating analyzer 27.

When a phase difference $\phi_p$ exists between the rotating analyzer 27 and the rotary encoder 28 and it is assumed that the output signal of the photodetector 30 is read out in synchronism with the output signal of the rotary encoder 28, an output $I_p$ which is obtained when the amplitude is assumed to be unity, can be described by $I_p = \sin^2(\omega t + \phi_p)$.

Figure 3:
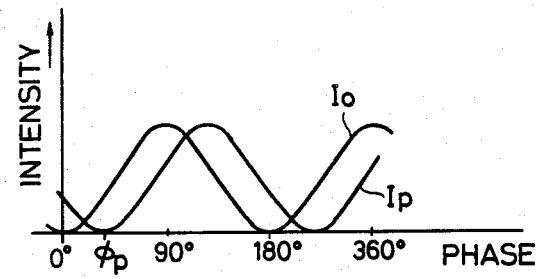
FIG. 3 is a graph for explaining the phase difference.
Figure 4:
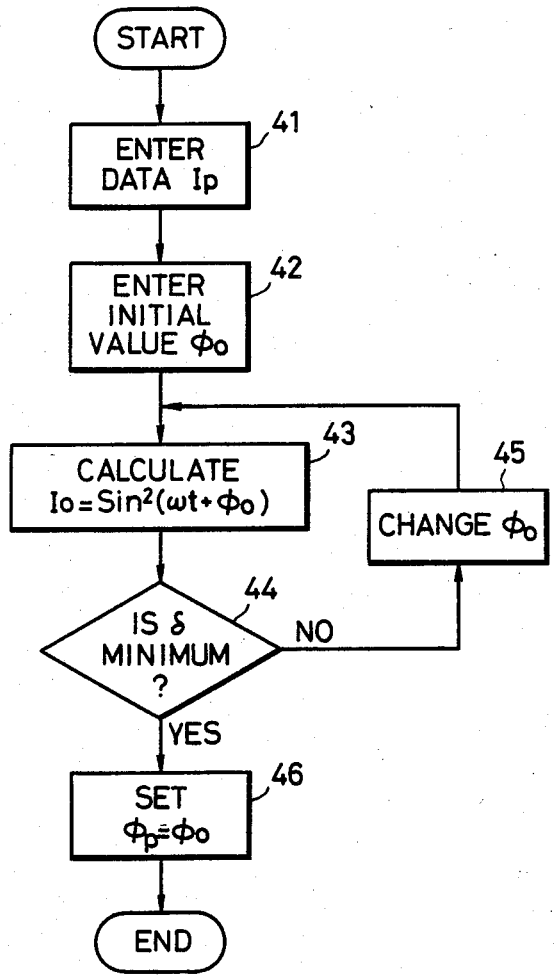
FIG. 4 is a flow chart for explaining the operation of a computer of the apparatus shown in FIG. 2.

FIG. 3 shows the outputs $I_o$ and $I_p$, and the phase difference $\phi_p$ exists between the two outputs $I_o$ and $I_p$. Hence, prior to measuring the film thickness, the phase difference $\phi_p$ is first detected. As shown in the flow chart of FIG. 4, when the operation of the computer 32 is started, a step 41 enters the output data $I_p$ of the photodetector 30 which is obtained through the A/D converter 31. Next, a step 42 enters an initial value $\phi_o$ of the phase difference. A step 43 calculates a theoretical value of $I_o = \sin^2(\omega t + \phi_o)$. Then, a step 44 compares the data $I_p$ and the theoretical value $I_o$ by use of the method of least squares. Deviations (differences) between the data $I_p$ which is a function and the theoretical value $I_o$ which is a function, are obtained and each of the deviations is squared. When a remainder obtained by adding the squared deviations is represented by $\delta$, the theoretical value $\phi_o$ is considered down to two places of decimals, and the theoretical value $\phi_o$ with which the remainder $\delta$ becomes a minimum is looked for. When the remainder $\delta$ is not a minimum, a step 45 changes the initial value $\phi_o$ of the phase difference, and the steps 43, 44, and 45 are repeated. On the other hand, when the remainder $\delta$ becomes a minimum, a step 46 uses the initial value $\phi_o$ which is obtained in the manner described above as the phase difference $\phi_p$ which is used when meauring the film thickness thereafter in the computer 32, and sets the phase difference $\phi_p$ ($\phi_o$) as the initial value for the calculation which is performed when measuring the film thickness. The detection of the phase difference and the setting of the initial value are completed by the operation described heretofore.

According to the present embodiment, the incident angle of the incident light need not be set again when measuring the film thickness by setting the incident angle $\theta$ to $\tan^{-1} n$ as previously proposed, because the detection of the phase difference is performed by setting the incident angle $\theta$ of the incident light to $\tan^{-1} n$. After performing the detection of the phase difference and setting the initial value for the calculation of the film thickness, it is possible to start the measurement of the film thickness without performing any adjustment of the incident angle.

The ellipsometer of the present embodiment is not limited to the application to the previously proposed film thickness measuring apparatus. In addition, the incident angle $\theta$ is not limited to a value described by $\tan^{-1} n$.

Further, in the present specification and claims, the measuring plate 10 and the substrate 10a described before will be referred to by a general term "sample".

Figure 5A:
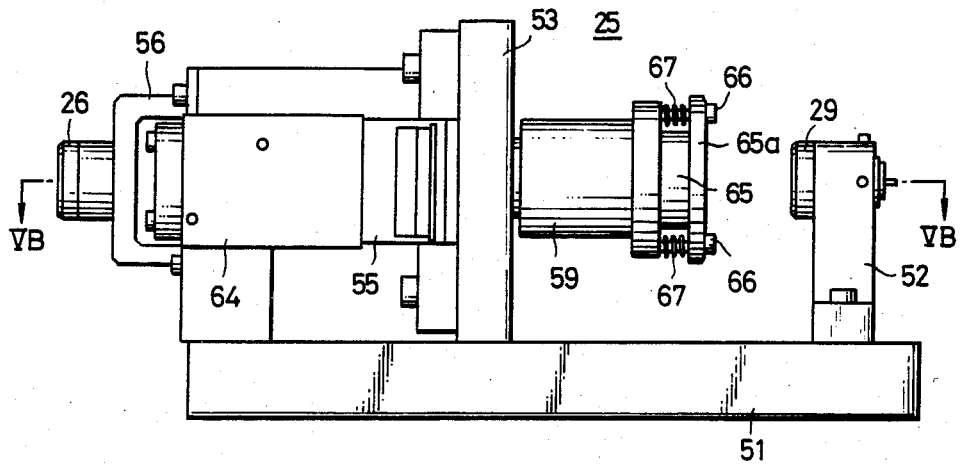
FIGS. 5A and 5B are a side view and a plan view in a horizontal cross section along a line VB—VB in FIG. 5A respectively showing an embodiment of a concrete construction of the ellipsometer according to the present invention.
Figure 5B:
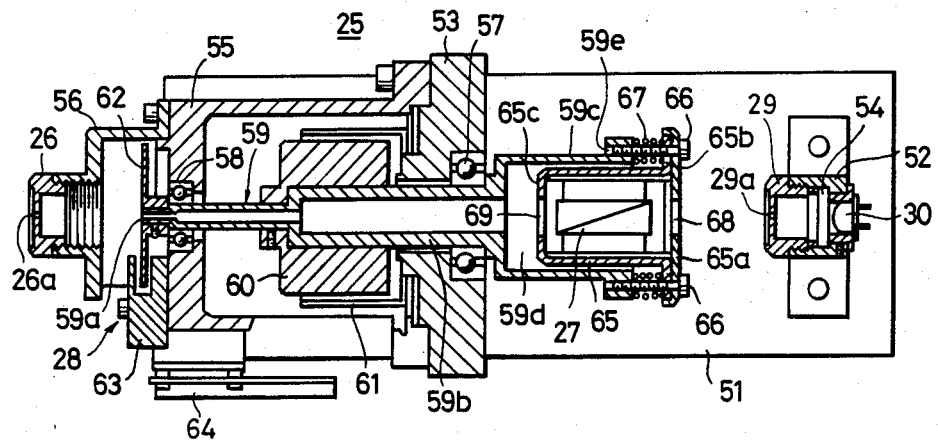

Next, a description will be given with respect to an embodiment of the concrete construction of the ellipsometer 25 by referring to FIGS. 5A and 5B. In FIGS. 5A and 5B, those parts which are the same as those corresponding parts in FIG. 2 are designated by the same reference numerals, and description thereof will be omitted.

A photodetector support 52 is fixed on a base 51. In addition, a support 53 for supporting the driving part of the rotating analyzer is fixed on the base 51. The photodetector 30, a filter 54, and the pinhole plate 29 having a pinhole 29a are fixed to the support 52.

A motor case 55 is mounted on the support 53. A pinhole plate holder 56 which is mounted with the pinhole plate 26 having a pinhole 26a, is fixed on the motor case 55.

A rotary shaft 59 rotatably supported by a bearing 57 which is provided on the support 53 and a bearing 58 which is provided on the motor case 55, has a hollow tube construction. The hollow part of the rotary shaft 59 constitutes an optical path.

A rotor (permanent magnet) 60 is fixed to an intermediate part 59b of the hollow rotary shaft 59. A stator 61 is provided in correspondence with the rotor 60. A rotary plate 62 of the rotary encoder 28 is fixed to a tip end part 59a of the hollow rotary shaft 59. When the rotary plate 62 of the rotary encoder 28 rotates unitarily with the hollow rotary shaft 59, the rotary encoder 28 generates from a signal generating part 63 an electrical signal responsive to the rotary angle of the hollow rotary shaft 59 in correspondence with a predetermined pattern provided on the rotary plate 62.

In the case where the rotary encoder 28 is an optical type rotary encoder, an optical pattern is provided along the circumference of the rotary plate 62 with a predetermined interval, and the signal generating part 63 is constituted by a light emitting part and a light receiving part for optically reading the optical pattern. On the other hand, in the case where the rotary encoder 28 is a magnetic type rotary encoder, a magnetic pattern is provided along the circumference of the rotary plate 62 with a predetermined interval, and the signal generating part 63 is designed so as to magnetically read the magnetic pattern and generate the electrical signal. The electrical signal generated from the rotary encoder 28 is amplified in an amplifier 64.

The rotating analyzer (Glan-Thompson prism) 27 is provided in an inner part 59d of the hollow part (space) in a rear end part 59c of the hollow rotary shaft 59, so that the optical axis of the rotating analyzer 27 coincides with the center of rotation of the hollow rotary shaft 59 and the rotating analyzer 27 can rotate unitarily with the hollow rotary shaft 59. In other words, the rotating analyzer 27 is provided in a drum-shaped holder 65. One end part 65b of the holder 65 is mounted on a rear end part 59e of the hollow rotary shaft 59 by a plurality of adjusting screws 66. Springs 67 fitted around the respective adjusting screws 66 exert urging forces which act in a direction so as to separate one end part of the holder 65 and the hollow rotary shaft 59. Hence, it is possible to easily adjust the center of the drum-shaped holder 65, that is, perform an adjustment so that the center of the rotating analyzer 27 coincides with the center of rotation of the hollow rotary shaft 59, by tightening or loosening the adjusting screws 66.

A hole 68 is formed in a central part of a bottom plate 65a of the holder 65. A hole 69 is formed in a central part of a top plate 65c of the holder 65.

The pinhole 29a of the pinhole plate 29 and the pinhole 26a of the pinhole plate 26 are arranged to lie on an extension of the center line of the hollow rotary shaft 59. Thus, the light reflected by the sample reaches the photodetector 30 by way of the pinhole 26a of the pinhole 26, the inner space of the hollow rotary shaft 59, the rotating analyzer 27, the hole 68, the pinhole 29a of the pinhole plate 29, and the filter 54 in this sequence.

According to the construction described heretofore, the rotating analyzer 27 having the optical axis which coincides with the center of rotation of the hollow rotary shaft 59, rotates unitarily with the hollow rotary shaft 59. In addition, the rotary encoder 28 which is provided coaxially to the hollow rotary shaft 59 also rotates unitarily with the hollow rotary shaft 59. For this reason, the rotary angle of the rotating analyzer 27 and the rotary angle of the rotary encoder 28 are constantly the same. Therefore, it is possible to easily obtain a highly accurate measured value by processing the signal which is generated in correspondence with the light which reaches the photodetector 30 by way of the optical path formed in the hollow part of the hollow rotary shaft 59.

Further, the present invention is not limited to these embodiments, but various variations and modifications may be made without departing from the scope of the present invention.

What is claimed is:

1. A rotating analyzer type ellipsometer comprising:
   a rotating analyzer for receiving light which is impinged on a sample with a predetermined incident angle and reflected by the sample;
   rotary phase detecting means provided so as to rotate unitarily with said rotating analyzer for generating a rotary phase signal as said rotary phase detecting means rotates;
   rotating means for rotating said rotating analyzer and said rotary phase detecting means;
   a photodetector for producing an output responsive to light which is passed through said rotating analyzer; and
   computer means for obtaining a phase difference between said rotating analyzer and said rotary phase detecting means from a phase difference $\phi_p$ with which a difference between an output $I_p$ of said photodetector and a theoretical value $I_o$ of said output $I_p$ becomes a minimum or substantially zero by entering into said computer means the output $I_p$ of said photodetector and calculating the theoretical value $I_o$ from an initial value $\phi_o$ of the phase difference $\phi_p$ while charging the value of the initial value $\phi_o$.

2. An ellipsometer as claimed in claim 1 in which said sample comprises a transparent film on top of a transparent substrate, said computer means setting the phase difference which is obtained as an initial value for a calculation of a film thickness.

3. An ellipsometer as claimed in claim 1 in which said predetermined incident angle $\theta$ is selected $\theta = \tan^{-1} n$, where n represents the refractive index of the sample.

4. An ellipsometer as claimed in claim 1 which further comprises a hollow rotary shaft rotated by said rotating means, said rotating analyzer being provided within said hollow rotary shaft with an optical axis of said rotating analyzer in coincidence with an axis of rotation of said hollow rotary shaft, said rotary phase detecting means comprising a rotary plate provided on said hollow rotary shaft and means for generating a rotary phase signal responsive to the rotation of said rotary plate, said hollow rotary shaft being arranged with the axis of rotation thereof in coincidence with a center of an optical path reaching said photodetector from said sample.

5. An ellipsometer as claimed in claim 4 in which said rotating means comprises a motor having a rotor thereof provided on said hollow rotary shaft so as to rotate unitarily with said hollow rotary shaft.

* * * * *